(12) United States Patent
Horstmeyer et al.

(10) Patent No.: US 11,213,245 B2
(45) Date of Patent: *Jan. 4, 2022

(54) SPATIAL AND TEMPORAL-BASED DIFFUSIVE CORRELATION SPECTROSCOPY SYSTEMS AND METHODS

(71) Applicant: HI LLC, Los Angeles, CA (US)

(72) Inventors: Roarke Horstmeyer, Durham, NC (US); Haojiang Zhou, Los Angeles, CA (US); Yuecheng Shen, Guangzhou University (CN); Haowen Ruan, Pasadena, CA (US)

(73) Assignee: HI LLC, Los Angeles, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/537,327

(22) Filed: Aug. 9, 2019

(65) Prior Publication Data

US 2019/0388018 A1 Dec. 26, 2019

Related U.S. Application Data

(63) Continuation of application No. 16/226,625, filed on Dec. 19, 2018, now Pat. No. 10,420,498.

(Continued)

(51) Int. Cl.
*A61B 5/00* (2006.01)
*A61B 5/026* (2006.01)
(Continued)

(52) U.S. Cl.
CPC .......... *A61B 5/4064* (2013.01); *A61B 5/0075* (2013.01); *A61B 5/029* (2013.01);
(Continued)

(58) Field of Classification Search
CPC ... A61B 5/4064; A61B 5/0075; A61B 5/0261; A61B 5/029; A61B 5/0402;
(Continued)

(56) References Cited

U.S. PATENT DOCUMENTS 4,018,534 A 4/1977 Thorn et al.
4,207,892 A 6/1980 Binder
(Continued)

FOREIGN PATENT DOCUMENTS

CN 200950235 9/2007
CN 107865635 4/2018
(Continued)

OTHER PUBLICATIONS

Ilev, Ilko K., and Ronald W. Waynant. "A simple submicron confocal microscope with a fiberoptic output." Review of Scientific Instruments 71, No. 11 (2000): 4161-4164.*

(Continued)

*Primary Examiner* — Carolyn A Pehlke
(74) *Attorney, Agent, or Firm* — ALG Intellectual Property, LLC

(57) ABSTRACT

A system includes an assembly, a pinhole array, and a processor. The assembly includes a K by L photodetector array comprising a plurality of photodetectors and configured to detect light that exits a body at a second location after the light enters the body at a first location different than the second location and scatters within the body, and output a plurality of electronic signals representative of the detected light as a function of time. The pinhole array has a K by L array of pinholes configured to be aligned with the photodetectors and is configured to allow a certain amount of light to be incident upon each of the photodetectors. The processor is configured to generate a correlation map that includes a plurality of spatiotemporal correlation measure values corresponding to the light detected by the photodetector array.

26 Claims, 13 Drawing Sheets

Related U.S. Application Data

(60) Provisional application No. 62/717,664, filed on Aug. 10, 2018, provisional application No. 62/687,657, filed on Jun. 20, 2018.

(51) Int. Cl.
*A61B 5/029* (2006.01)
*A61B 5/318* (2021.01)
*A61B 5/369* (2021.01)

(52) U.S. Cl.
CPC .......... *A61B 5/0261* (2013.01); *A61B 5/318* (2021.01); *A61B 5/369* (2021.01); *A61B 5/6814* (2013.01); *A61B 5/7246* (2013.01)

(58) Field of Classification Search
CPC ... A61B 5/0476; A61B 5/6814; A61B 5/7246; A61B 5/14553; A61B 5/72; A61B 2562/0238; G06F 3/015; G06F 3/01; G06F 17/10; G01J 3/10; G01J 3/2889; G01J 3/4406; G01N 21/4795; G01N 21/64
See application file for complete search history.

(56) References Cited

U.S. PATENT DOCUMENTS

| | | |
|---|---|---|
| 4,281,645 A | 8/1981 | Jobsis |
| 4,321,930 A | 3/1982 | Jobsis |
| 4,515,165 A | 5/1985 | Carroll |
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,240,309 B1 | 5/2001 | Yamashita et al. |
| 6,384,663 B2 | 5/2002 | Cova et al. |
| 6,541,752 B2 | 4/2003 | Zappa et al. |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | Mcgarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara'et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |

(56) References Cited

U.S. PATENT DOCUMENTS

| | | |
|---|---|---|
| 10,515,993 B2 | 12/2019 | Field et al. |
| 10,533,893 B2 | 1/2020 | Leonardo |
| 10,558,171 B2 | 2/2020 | Kondo |
| 10,594,306 B2 | 3/2020 | Dandin |
| 10,627,460 B2 | 4/2020 | Alford et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 2004/0057478 A1 | 3/2004 | Saito |
| 2004/0078216 A1 | 4/2004 | Toto |
| 2004/0160996 A1 | 8/2004 | Giorgi et al. |
| 2005/0061986 A1 | 3/2005 | Kardynal et al. |
| 2006/0197452 A1 | 9/2006 | Zhang |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0163775 A1 | 6/2009 | Barrett |
| 2009/0313048 A1 | 12/2009 | Kahn et al. |
| 2010/0210952 A1 | 8/2010 | Taira et al. |
| 2011/0208675 A1 | 8/2011 | Shoureshi et al. |
| 2012/0029304 A1 | 2/2012 | Medina et al. |
| 2012/0101838 A1 | 4/2012 | Lingard et al. |
| 2013/0030267 A1 | 1/2013 | Lisogurski |
| 2013/0032713 A1 | 2/2013 | Barbi et al. |
| 2013/0144644 A1 | 6/2013 | Simpson |
| 2013/0221221 A1 | 8/2013 | Bouzid et al. |
| 2013/0342835 A1 | 12/2013 | Blacksberg |
| 2014/0027607 A1 | 1/2014 | Mordarski et al. |
| 2014/0066783 A1 | 3/2014 | Kiani |
| 2014/0185643 A1 | 7/2014 | Mccomb et al. |
| 2014/0191115 A1 | 7/2014 | Webster et al. |
| 2014/0211194 A1 | 7/2014 | Pacala et al. |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | Mcgarvey et al. |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0014066 A1* | 1/2017 | Culver ............... G06T 7/0012 |
| 2017/0030769 A1 | 2/2017 | Clemens et al. |
| 2017/0047372 A1 | 2/2017 | Mcgarvey et al. |
| 2017/0052065 A1 | 2/2017 | Sharma et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0167211 A1 | 6/2019 | Everman et al. |
| 2019/0175068 A1 | 6/2019 | Everdell |
| 2019/0200888 A1 | 7/2019 | Poltorak |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0182692 A1 | 6/2020 | Lilic |
| 2020/0191883 A1 | 6/2020 | Bhattacharyya |
| 2020/0196932 A1 | 6/2020 | Johnson |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |

(56) References Cited

U.S. PATENT DOCUMENTS

| | | |
|---|---|---|
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |

FOREIGN PATENT DOCUMENTS

| | | |
|---|---|---|
| EP | 0656536 | 4/2004 |
| EP | 3487072 | 5/2019 |
| WO | 8804034 | 6/1988 |
| WO | 1999053577 | 10/1999 |
| WO | 2008144831 | 12/2008 |
| WO | 2015052523 | 4/2015 |
| WO | 2015109005 | 7/2015 |
| WO | 2016164900 | 10/2016 |
| WO | 2017130682 | 8/2017 |
| WO | 2017147539 | 8/2017 |
| WO | 2018090040 | 5/2018 |

OTHER PUBLICATIONS

Dabbs, Tim, and Monty Glass. "Single-mode fibers used as confocal microscope pinholes." Applied optics 31, No. 6 (1992): 705-706.*
Non-Final Office Action received in U.S. Appl. No. 16/226,625 dated Mar. 19, 2019.
SPC3 Single Photon Counting Camera, Micro Photon Devices S.r.l. SPC3 User Manual Version 1.1.0—Nov. 2015.
Boas, et al., Establishing the diffuse correlation spectroscopy signal relationship with blood flow, Neurophotonics, 3(3), 031412 (2016), www.Neurophotonics.SPIEDigitalLibrary.org, 2016, 1-9.
Boas, D. A. et al., Scattering and Imaging with Diffusing Temporal Field Correlations, The American Physical Society. Physical Review Letters, vol. 75, No. 9, Aug. 28, 1995.
Buckley, Erin M. et al., Diffuse correlation spectroscopy for measurement of cerebral blood flow: future prospects, Neurophotonics vol. 1(1), 011009 (Jul.-Sep. 2014). https://www.spiedigitallibrary.org/journals/Neurophotonics.
Dietsche, G. et al., Fiber-based multispeckle detection for time-resolved diffusing-wave spectroscopy: characterization and application to blood flow detection in deep tissue, Applied Optics 46 (2007), 35, pp. 8506-8514.
Hebert, et al., Spatiotemporal image correlation spectroscopy (STICS) theory, verification, and application to protein velocity mapping in living CHO cells, Biophysical journal 88, No. 5 (2005): 3601-3614.
Kheng, et al., Image Processing, https://www.comp.nus.edu.sg/~cs4243/lecture/imageproc.pdf, Mar. 9, 2014.
Li, Jun et al., Pulsation-resolved deep tissue dynamics measured with diffusing-wave spectroscopy, Aug. 21, 2006 / vol. 14, No. 17 / Optics Express 7841.
Pagliazzi, M. et al., Time domain diffuse correlation spectroscopy with a high coherence pulsed source: in vivo and phantom results, vol. 8, No. 11 / Nov. 1, 2017 / Biomedical Optics Express 5311.
Sneha, et al., Understanding Correlation, https://www.allaboutcircuits.com/technical-articles/understanding-correlation/, Jan. 4, 2017.
Sutin, Jason et al., Time-domain diffuse correlation spectroscopy, vol. 3, No. 9 / Sep. 2016 / Optica 1006-1013.
Wang, Detian et al., Fast blood flow monitoring in deep tissues with real-time software correlators, Optical Society of America, Mar. 1, 2016 / vol. 7, No. 3 / DOI:10.1364/BOE.7.000776 / Biomedical Optics Express 776.
Zarychta, Katarzyna et al., Time-resolved diffusing wave spectroscopy with a CCD camera, Aug. 2, 2010 / vol. 18, No. 16 / Optics Express 16289.
Zhou, Chao et al., Diffuse optical correlation tomography of cerebral blood flow during cortical spreading depression in rat brain, Optical Society of America, Feb. 6, 2006 / vol. 14, No. 3 / Optics Express 1125.
Zucconi, et al., The Autocarrelation Function, https://www.alanzucconi.com/2016/06/06/autocorrelation-function/, Jun. 6, 2016.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Mita, et al., "High-Speed and Compact Quenching Circuit for Single-Photon Avalanche Diodes", IEEE Transactions on Instrumentation and Measurement, vol. 57, No. 3, Mar. 2008. pp. 543-547.
Puszka, et al., "Time-resolved diffuse optical tomography using fast-gated single-photon avalanche diodes", Biomedical optics express, 2013, vol. 4, No. 8, pp. 1351-1365 (Year: 2013).
Takai, et al., "Single-Photon Avalanche Diode with Enhanced NIR-Sensitivity for Automotive LIDAR Systems", Sensors, 2016, 16(4): 459, pp. 1-9 (Year: 2016).
Xu, et al., "A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.

* cited by examiner

SPATIAL AND TEMPORAL-BASED DIFFUSIVE CORRELATION SPECTROSCOPY SYSTEMS AND METHODS

RELATED APPLICATIONS

This application is a continuation application of U.S. patent application Ser. No. 16/226,625, filed on Dec. 19, 2018, which claims priority under 35 U.S.C. § 119(e) to U.S. Provisional Patent Application No. 62/687,657, filed on Jun. 20, 2018, and to U.S. Provisional Patent Application No. 62/717,664, filed on Aug. 10, 2018. These applications are incorporated herein by reference in their respective entireties.

BACKGROUND INFORMATION

Detection of brain activity is useful for medical diagnostics, imaging, neuroengineering, brain-computer interfacing, and a variety of other diagnostic and consumer-related applications. For example, cerebral blood flow ensures the delivery of oxygen and needed substrates to tissue, as well as removal of metabolic waste products. Thus, detection and quantification of cerebral blood flow is useful for diagnosis and management of any brain injury or disease associated with ischemia or inadequate vascular autoregulation.

As another example, there is an increasing interest in measuring event-related optical signals (also referred to as fast-optical signals). Such signals are caused by changes in optical scattering that occur when light propagating through active neural tissue (e.g., active brain tissue) is perturbed through a variety of mechanisms, including, but not limited to, cell swelling, cell volume change, cell displacement, changes in membrane potential, changes in membrane geometry, ion redistribution, birefringence changes, etc. Because event-related optical signals are associated with neuronal activity, rather than hemodynamic responses, they may be used to detect brain activity with relatively high temporal resolution.

Diffusive correlation spectroscopy (DCS), also referred to as diffusive wave spectroscopy (DWS), is a non-invasive optical procedure that has been shown to be effective in measuring some types of brain activity, such as cerebral blood flow. A conventional DCS system directs high coherence light (e.g., a laser) at a head of a subject. Some of the light propagates through the scalp and skull and into the brain where it is scattered by moving red blood cells in tissue vasculature before exiting the head. This dynamic scattering from moving cells causes the intensity of the light that exits the head to temporally fluctuate. To detect these temporal fluctuations, a conventional DCS system includes a photodetector and a correlator. The photodetector detects individual photons in the light that exits the head. The correlator keeps track of the arrival times of all photons detected by the photodetector and derives an intensity correlation function from temporal separations between the photons. This intensity correlation function is representative of the temporal fluctuations of the intensity of the light that exits the head, and is therefore also indicative of blood flow.

A conventional photodetector requires approximately one second to acquire enough signal for a meaningful measurement by a conventional DCS system. This is sufficient to detect changes in blood flow, which occur at relatively slow time scales (e.g., one second or more). However, conventional DCS systems do not operate fast enough to detect event-related optical signals caused, for example, by cellular activity, which occurs at a much faster rate than changes in blood flow.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
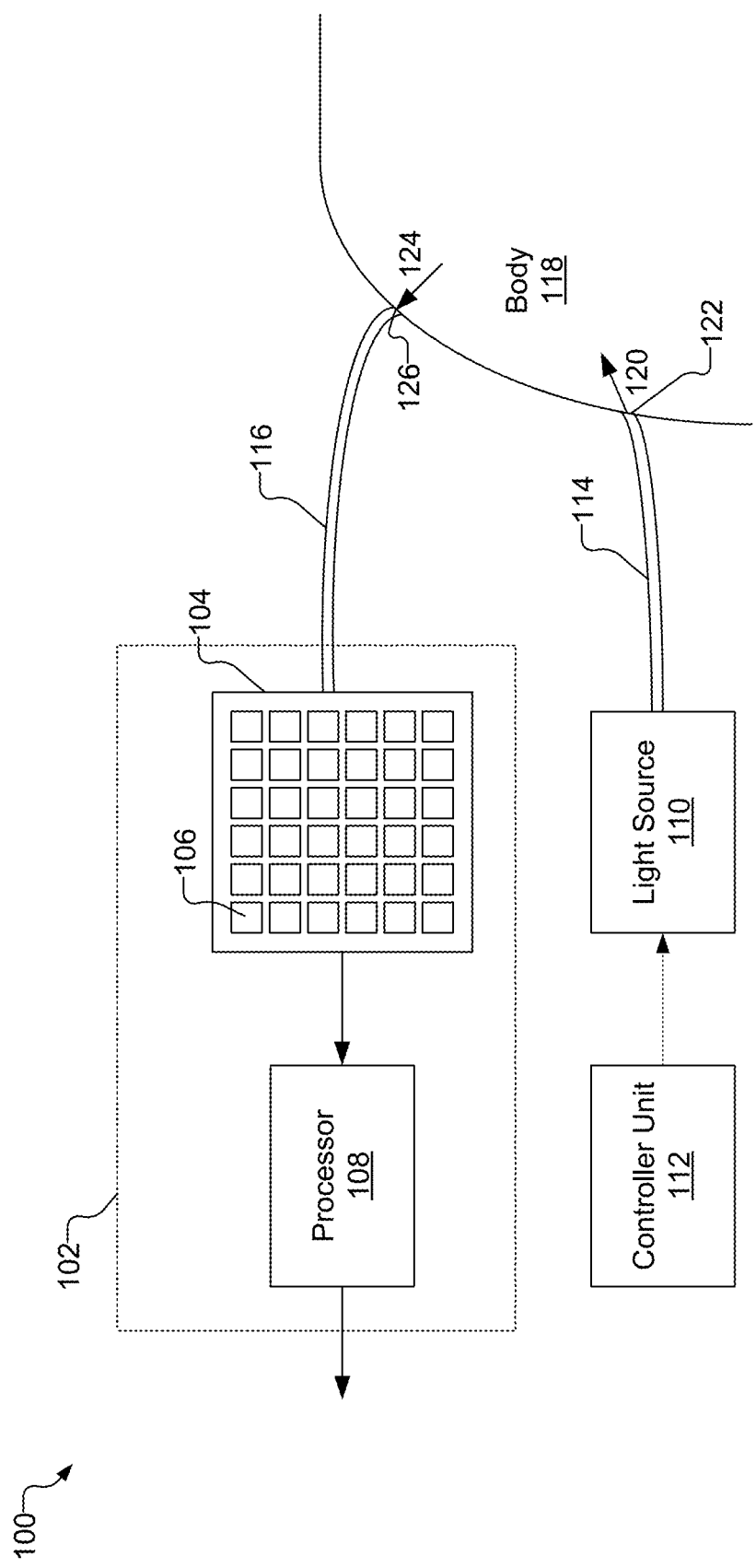
FIG. 1 shows an exemplary configuration in which a DCS system is configured to determine spatiotemporal correlation measurement values according to principles described herein.

Spatial and temporal-based DCS systems and methods are described herein. In some examples, as will be described in more detail below, a light source (e.g., a laser diode) generates coherent light that enters a body (e.g., a head of a subject) at an input location. The incident light scatters through many different optical paths within the body. Because of its high coherence, the light emerges from the body with the ability to interfere with itself to produce an interference pattern at one or more output locations. This interference pattern takes the form of a fully developed speckle pattern at the one or more output locations. A DCS system as described herein may determine spatiotemporal correlation measurement values representative of speckle decorrelation (i.e., how speckles within the speckle pattern vary with respect to time and space).

To this end, the DCS system includes a K by L photodetector array and a processor coupled to an output of the photodetector array. The photodetector array includes a plurality of photodetectors each configured to detect light that emerges from the body after it has scattered within the body. Each photodetector is further configured to output an electronic signal representative of the detected light as a function of time. Hence, the photodetector array as a whole is configured to output a plurality of electronic signals representative of the detected light as a function of time.

The processor is configured to sample the electronic signals output by the photodetector array at a plurality of delay times during a predetermined time period to generate a sequence of frames each corresponding to a different delay time in the plurality of delay times. Each of the frames includes K times L digital sample values at K by L pixel locations that correspond to locations of the photodetectors within the photodetector array.

The processor is further configured to apply a plurality of temporal-based and spatial-based correlation measurement operations to the sample values in each of the frames. Based on the application of the temporal-based and spatial-based correlation measurement operations to the sample values, the processor is configured to generate a plurality of spatiotemporal correlation measure values for the light detected by the photodetector array. These spatiotemporal correlation measure values represent speckle decorrelation associated with the light detected by the photodetector array. The processor is further configured to include the plurality of spatiotemporal correlation measure values in a correlation map that corresponds to a predetermined delay time interval. The predetermined delay time interval represents a difference between two delay times within the plurality of delay times.

By applying both temporal-based and spatial-based correlation measurement operations, as opposed to only temporal-based measurement operations as applied in conventional DCS systems, the systems and methods described herein provide additional useful information regarding the decorrelation process of coherent light that exits the body after scattering within the body. For example, the spatiotemporal correlation measure values generated by the systems and methods described herein may provide more accurate, useful, and distinguishing measures of brain activity than correlation measures generated by conventional DCS systems that are only temporally based.

Moreover, by applying both temporal-based and spatial-based correlation measurement operations, the systems and methods described herein can relax sampling requirements over time. For example, decorrelation rates in the human head typically require sampling at 1 MHz when only temporal-based correlation measurement operations are performed. However, by also performing spatial-based correlation measurement operations, the systems and methods described herein can obtain accurate measurements of decorrelation at sample rates that are much lower (e.g., around 200 kHz).

Furthermore, by using a photodetector array that includes many (e.g., 100 to 100,000) photodetectors, as opposed to a single photodetector as used in conventional DCS systems, the systems and methods described herein can dramatically speed up the sampling rate of DCS into the sub-millisecond range. By speeding up acquisition into this range, the systems and methods described herein can sample at rates that are sufficient to resolve event-related optical signals (also referred to as fast-optical signals). Such signals are caused by changes in optical scattering that occur when light propagating through active neural tissue (e.g., active brain tissue) is perturbed through a variety of mechanisms, including, but not limited to, cell swelling, cell volume change, cell displacement, changes in membrane potential, changes in membrane geometry, ion redistribution, birefringence changes, etc. Because event-related optical signals are associated with neuronal activity, rather than hemodynamic responses, they may be used to detect brain activity with relatively high temporal resolution. Resolution of event-related optical signals is described more fully in U.S. Provisional Application No. 62/692,074, filed Jun. 29, 2018, the contents of which are hereby incorporated by reference in their entirety.

These and other benefits and/or advantages that may be provided by the systems and methods described herein will be made apparent by the following detailed description.

FIG. 1 shows an exemplary configuration 100 in which a DCS system 102 is configured to determine spatiotemporal correlation measurement values representative of speckle decorrelation. As shown, DCS system 102 includes a photodetector array 104 composed of a plurality of individual photodetectors (e.g., photodetector 106) and a processor 108 coupled to an output of photodetector array 104. Other components included in configuration 100 (e.g., a light source 110, a controller unit 112, and optical fibers 114 and 116) are not shown to be included in DCS system 102 in FIG. 1. However, one or more of these components may, in certain embodiments, be considered to be a part of DCS system 102.

Light source 110 may be implemented by any suitable component configured to generate and emit high coherence light (e.g., light that has a coherence length of at least 5 centimeters) at a predetermined center wavelength. For example, light source 110 may be implemented by a high-coherence laser diode.

Light source 110 is controlled by controller unit 112, which may be implemented by any suitable computing device, integrated circuit, and/or combination of hardware and/or software as may serve a particular implementation. In some examples, controller unit 112 is configured to control light source 110 by turning light source 110 on and off and/or setting an intensity of light generated by light source 110. Controller unit 112 may be manually operated by a user, or may be programmed to control light source 110 automatically.

Light emitted by light source 110 travels via an optical fiber 114 (e.g., a single-mode fiber or a multi-mode fiber) to a body 118 of a subject. In some implementations, body 118 is a head or any other body part of a human or other animal. Alternatively, body 118 may be a non-living object. For illustrative purposes, it will be assumed in the examples provided herein that body 118 is a human head.

As indicated by arrow 120, the light emitted by light source 110 enters body 118 at a first location 122 on body 118. To this end, a distal end of fiber 114 may be positioned at (e.g., right above or physically attached to) first location 122 (e.g., to a scalp of the subject). In some examples, the light may emerge from fiber 114 and spread out to a certain spot size on body 118 to fall under a predetermined safety limit.

After the light enters body 118, the light scatters through many different optical paths within body 118. The light emerges from body 118 at various locations. For example, as illustrated by arrow 124, the light may exit from body 118 at location 126, which is different than location 122. Because of its high coherence, the light may interfere with itself to produce an interference pattern in the form of a fully developed speckle pattern at location 126.

As shown, a proximal end of optical fiber 116 (e.g., a multi-mode optical fiber) is positioned at (e.g., right above or physically attached to) output location 126. In this manner, optical fiber 116 may collect light as it exits body 124 at location 126 and carry the light to photodetector array 104. The light may pass through one or more lenses and/or other optical elements (not shown) that direct the light onto each of the photodetectors 106 included in photodetector array 104.

Figure 2:
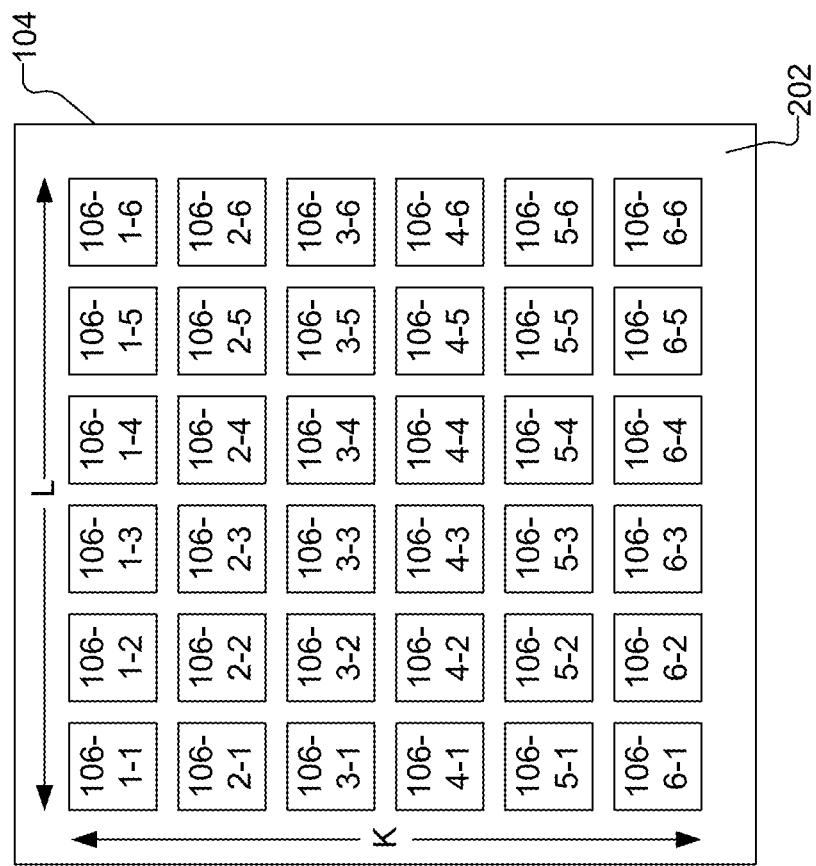
FIG. 2 illustrates an exemplary photodetector array according to principles described herein.

FIG. 2 illustrates photodetector array 104 in more detail. As shown, photodetector array includes a plurality of photodetectors 106 arranged in a K by L array. In the example of FIG. 2, K and L are both equal to six. However, it will be recognized that photodetector array 104 may have any other suitable dimension where K times L is greater than one. In some examples, photodetector array 104 includes between 10 and 100,000 photodetectors.

Each photodetector 106 is labeled in FIG. 2 with indices that indicate a position (i.e., a row number and a column number) of the photodetector within photodetector array 104. For example, photodetector 106-1-1 is located in the first row and first column of photodetector array 104 and photodetector 106-6-6 is located in the sixth row and sixth column of photodetector array 104. As shown, each photodetector 106 may be disposed on a surface 202. Surface 202 may be implemented by a printed circuit board (PCB), an ASIC, or any other suitable surface. In some examples, each photodetector 106 may be created via lithography on a silicon substrate, and then wire-bonded and packaged like other similar CMOS image chips.

Photodetectors 106 may each be implemented by any suitable circuit configured to detect individual photons of light incident upon photodetectors 106. For example, each photodetector 106 may be implemented by a single photon avalanche diode (SPAD) circuit. Unlike conventional SPAD circuits, the SPAD circuits that implement photodetectors 106 operate in a freely-running configuration, as opposed to a time-correlated single-photon-counting configuration.

Photodetectors 106 may each detect light that exits the body at location 126 and output an electronic signal representative of the detected light as a function of time. Because there are K times L photodetectors 106, photodetector array 104 outputs K times L electronic signals, where each photodetector 106 generates a different one of the K times L electronic signals.

To illustrate, a photodetector (e.g., photodetector 106-1-1) may detect light and output an electronic signal representative of the detected light as a function of time by detecting individual photons as they arrive at the photodetector and outputting an analog pulse each time a photon is detected. Hence, the electronic signal may include a series of pulses, where each pulse represents an arrival time of a photon. Alternatively, the photodetector may track how many photons arrive at the photodetector during a particular time interval (e.g., 10 microseconds) and output a count value representative of this number. In this case, the electronic signal output by the photodetector may include a series of values each representative of a number of photons that hit the photodetector during subsequent time intervals.

Photodetectors 106 may be configured to operate in a freely running mode as opposed to a time-correlated single photon counting mode. In other words, the photodetectors 106 used in connection with the systems and methods described herein may simply output pulses when photons are detected without having to determine actual arrival times of the photons. This advantageously reduces the complexity and cost of the photodetectors 106 compared to conventional DCS systems that use time-of-flight optical measurement systems for in-vivo detection.

Processor 108 may be implemented by one or more physical processing (e.g., computing) devices. In some examples, processor 108 may execute software configured to perform one or more of the operations described herein. Processor 108 is configured to sample the electronic signals output by photodetector array 104 at N delay times during a time period T to generate a sequence of N frames. The time period T may be of any suitable duration (e.g., less than or equal to one microsecond). N may also have any suitable value greater than one. For example, N may be between 10 and 100,000.

Figure 3:
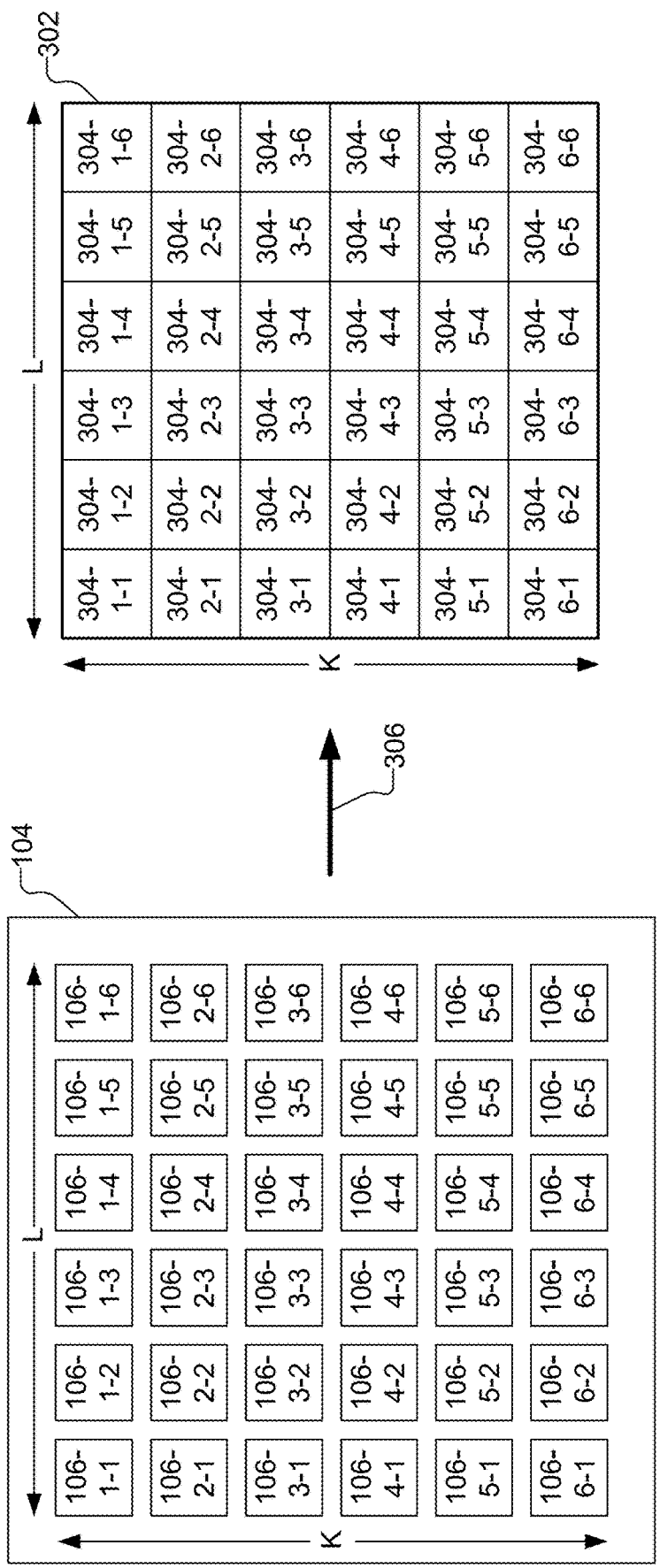
FIG. 3 shows a relationship between a photodetector array and a frame according to principles described herein.

FIG. 3 shows a relationship between photodetector array 104 and a frame 302 included in the N frames generated by processor 108 sampling the electronic signals output by photodetector array 104 at a particular delay time. Each of the N frames generated by processor 108 has the same dimensions and structure as frame 302.

As shown, frame 302 has K by L pixel locations 304. Each pixel location 304 is labeled in FIG. 3 with indices that indicate a position (i.e., a row number and a column number) of the pixel location 304 within frame 302. For example, pixel location 304-1-1 is located in the first row and first column of frame 302 and pixel location 304-6-6 is located in the sixth row and sixth column of frame 302. Each pixel location 304 corresponds to a location of a particular photodetector 106 in photodetector array 104. For example, pixel location 304-1-1 corresponds to a location of photodetector 106-1-1 in photodetector array 104, pixel location 304-1-2 corresponds to a location of photodetector 106-1-2 in photodetector array 104, etc.

As mentioned, frame 302 is generated by processor 108 sampling the electronic signals output by photodetector array 104 at a particular delay time. This sampling is represented in FIG. 3 by arrow 306 and may be performed in accordance with any suitable signal processing heuristic. The sampling generates a plurality of digital sample values that are included in frame 302 at pixel locations 304. For example, frame 302 includes a digital sample value at pixel location 304-1-1 of an electronic signal output by photodetector 106-1-1, a digital sample value at pixel location 304-1-2 of an electronic signal output by photodetector 106-1-2, etc.

Processor 108 may apply a plurality of temporal-based and spatial-based correlation measurement operations to the sample values in each of the N frames generated by processor 108. Based on the application of the temporal-based and spatial-based correlation measurement operations to the sample values, processor 108 may generate a plurality of spatiotemporal correlation measure values for the light detected by photodetector array 104. Processor 108 may include the plurality of spatiotemporal correlation measure values in one or more correlation maps that each corresponding to a different predetermined delay time interval.

Figure 4:
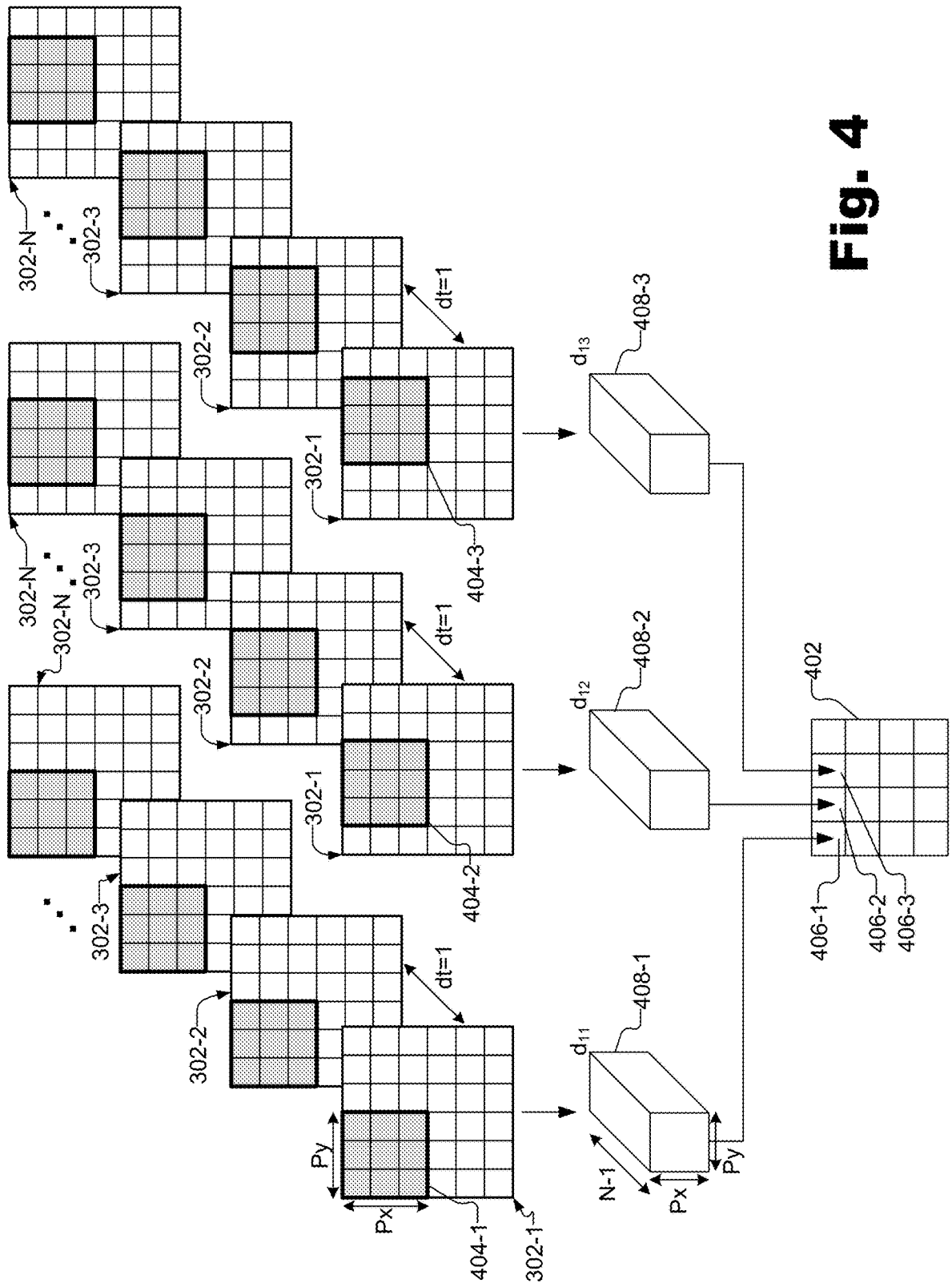
FIG. 4 illustrates an exemplary heuristic that may be performed by a processor on a sequence of frames to generate a correlation map according to principles described herein.

FIG. 4 illustrates an exemplary heuristic that may be performed by processor 108 on a sequence of frames 302 to generate a correlation map 402 that corresponds to a delay time interval of one, where the delay time interval is defined as an integer number of delay times between frames, from which frames will be considered to generate a particular correlation measurement. As shown, the sequence of frames 302 includes frames 302-1 through 302-N. Each frame 302 is generated by processor 108 sampling the electronic signals output by photodetector array 104 at a particular delay time. For example, frame 302-1 is generated by processor 108 sampling the electronic signals output by photodetector array 104 at a first delay time, frame 302-2 is generated by processor 108 sampling the electronic signals output by photodetector array 104 at a second delay time immediately subsequent to the first delay time, etc. Each frame 302 is therefore temporally spaced from a subsequent frame 302 by a delay time interval (dt) of one (i.e., dt=1). The same sequence of frames 302 is shown three different times in FIG. 4 to illustrate how frames 302 are processed by processor 108, as will be made apparent below.

In the example of FIG. 4, processor 108 generates correlation map 402 by applying a plurality of temporal-based and spatial-based correlation measurement operations to sample values included in a plurality of overlapping pixel regions (e.g., pixel regions 304-1 through 304-3). The overlapping pixel regions 304 are shaded and surrounded by a thick border for illustrative purposes. In the particular example of FIG. 4, each pixel region 404 includes a three by three block of pixel locations. For example, pixel region 404-1 includes pixel locations in the top-left corner of frame 302-1. With reference to FIG. 3, these pixel locations include pixel locations 304-1-1, 304-1-2, 304-1-3, 304-2-1, 304-2-2, 304-2-3, 304-3-1, 304-3-2, and 304-3-3. As shown, pixel region 404-2 overlaps with and is offset from pixel region 404-1 by one pixel column to the right. Likewise, pixel region 404-3 overlaps with and is offset from pixel region 404-2 by one pixel column to the right. Other pixel regions of the same size (e.g., a pixel region that overlaps with and is offset from pixel region 404-1 by one row down) are not specifically highlighted in FIG. 4. However, it will be recognized that in the example of FIG. 4, sixteen three by three pixel regions fit within each of frames 302.

It will be recognized that while three by three pixel regions are shown in FIG. 4, the pixel regions may alternatively be of any other suitable size. In general, each pixel region may include Px by Py pixel locations, where Px times Py is greater than one.

Correlation map 402 includes a plurality of locations 406 (e.g., locations 406-1 through 406-3) that each correspond to a particular one of the overlapping pixel regions 404 (i.e., each location 406 includes a spatiotemporal correlation measure value corresponding to one of the overlapping pixel regions 404). For example, in the example of FIG. 4, location 406-1 corresponds to pixel region 404-1, location 406-2 corresponds to pixel region 404-2, and location 406-3 corresponds to pixel region 404-3. Hence, the size of correlation map 402 depends on the number of overlapping pixel regions 404 included in each frame 302. In the example of FIG. 4, because there are a total of sixteen possible overlapping pixel regions 404 in frames 302, correlation map 402 may include sixteen locations 406, arranged in a four by four matrix.

Exemplary temporal-based and spatial-based correlation measurement operations that may be performed by processor 108 with respect to pixel region 404-1 will now be described. Because correlation map 402 corresponds to a delay time interval of one, processor 108 may first apply a plurality of temporal-based correlation measurement operations to sample values included in corresponding pixel locations within pixel region 404-1 for each subsequent and overlapping pair of frames 302 (i.e., frames 302-1 and 302-2, frames 302-2 and 302-3, etc.).

Figure 5:
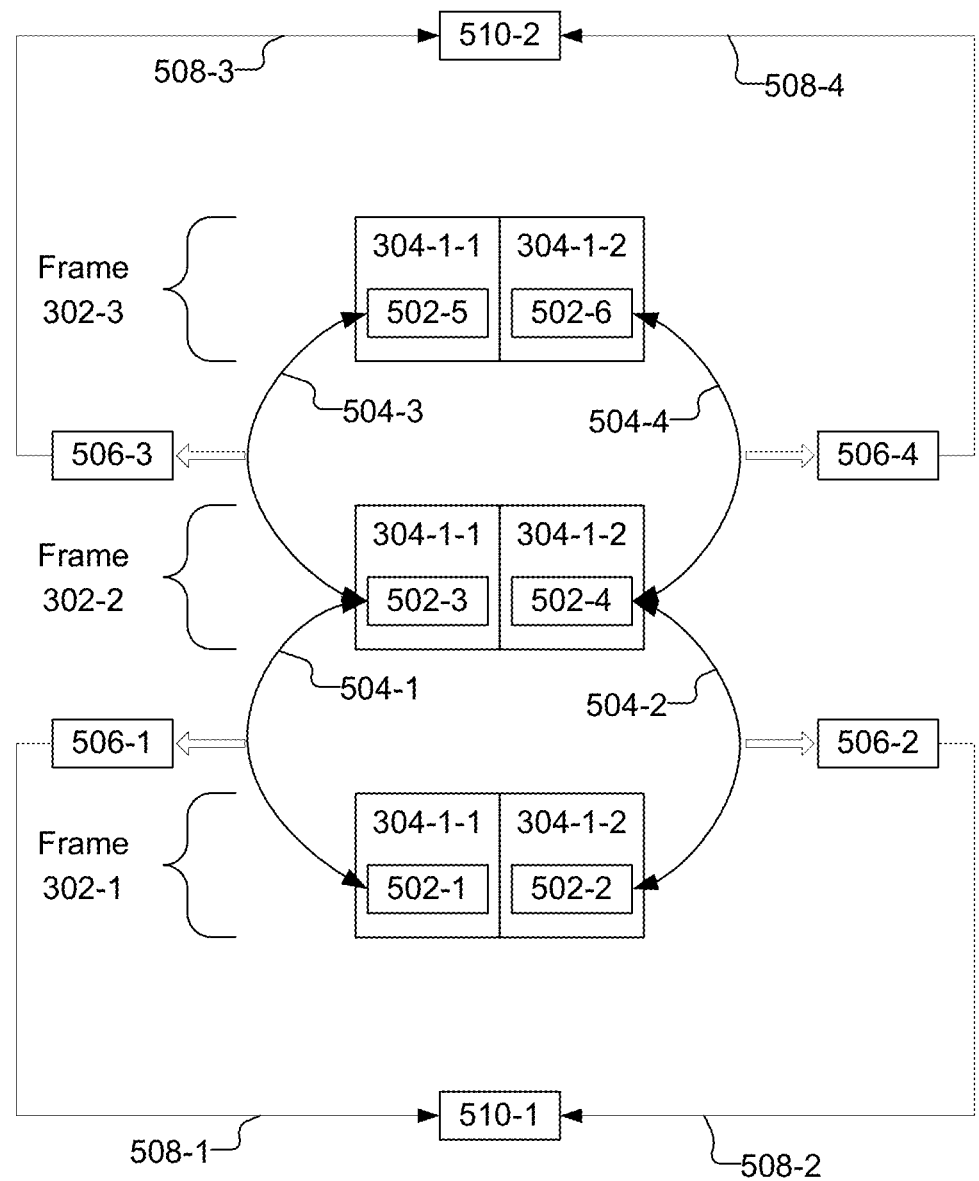
FIG. 5 shows pixel locations included in a pixel region of a frame according to principles described herein.

To illustrate, FIG. 5 shows pixel locations 304-1-1 and 304-1-2 included in pixel region 404-1 of each of frames 302-1 through 302-3. Only two of the nine pixel locations of pixel region 404-1 are shown in FIG. 5 for illustrative purposes. As shown, frames 302 each include a sample value 502 at each of pixel locations 304-1-1 and 304-1-2. For example, frame 302-1 includes a sample value 502-1 at pixel location 304-1-1 and a sample value 502-2 at pixel location 304-1-2, frame 302-2 includes a sample value 502-3 at pixel location 304-1-1 and a sample value 502-4 at pixel location 304-1-2, and frame 302-3 includes a sample value 502-5 at pixel location 304-1-1 and a sample value 502-6 at pixel location 304-1-2.

As represented by arrow 504-1, processor 108 may apply a first temporal-based correlation measurement operation to frames 302-1 and 302-2 by processing sample value 502-1 with sample value 502-3 to obtain a first temporal correlation measure value 506-1 for pixel location 304-1-1. Likewise, as represented by arrow 504-2, processor 108 may apply a second temporal-based correlation measurement operation to frames 302-1 and 302-2 by processing sample value 502-2 with sample value 502-4 to obtain a temporal correlation measure value 506-2 for pixel location 304-1-2.

Processor 108 may similarly apply temporal-based correlation measurement operation to frames 302-2 and 302-3. For example, as represented by arrow 504-3, processor 108 may apply a first temporal-based correlation measurement operation to frames 302-2 and 302-3 by processing sample value 502-3 with sample value 502-5 to obtain a second temporal correlation measure value 506-3 for pixel location 304-1-1. Likewise, as represented by arrow 504-4, processor 108 may apply a second temporal-based correlation measurement operation to frames 302-2 and 302-3 by processing sample value 502-4 with sample value 502-6 to obtain a second temporal correlation measure value 506-4 for pixel location 304-1-2.

Processor 108 may similarly process sample values included in each of the other corresponding pixel locations included in pixel region 404-1 of frames 302-1 and 302-2, frames 302-2 and 302-3, etc. until processor 108 has obtained temporal correlation measurement values 506 for each pixel location of pixel region 404-1 in each subsequent and overlapping pair of frames 302.

Processor 108 may process a first sample value (e.g., sample value 502-1) with a second sample value (e.g., sample value 502-3) to obtain a temporal correlation measurement value (e.g., temporal correlation measurement value 506-1) in any suitable manner. For example, processor 108 may multiply the first sample value with the second sample value. Processor 108 may also process N different sample values in a repeated manner to obtain a temporal correlation measurement value. For example, processor 108 may multiply the first sample value with the second sample value, then multiply the second sample value with the third sample value, etc., and finally multiply the N−1th sample value with the Nth sample value, and then take the average of all of the N−1 products to obtain a temporal correlation measurement value. Example values of N may range from 10 to 10,000. Additional or alternative temporal-based correlation measurement operations may be performed on the first and second sample values, or on the N sample values, to obtain a temporal correlation measurement value as may serve a particular implementation.

With reference again to FIG. 4, processor 108 may include (e.g., store) the obtained temporal correlation measurement values 506 for each pixel location of pixel region 404-1 in a datacube 408-1 (also referred to as datacube $d_{11}$) corresponding to pixel region 404-1. As shown, datacube 408-1 is a three-dimensional array of temporal correlation measure values, and has dimensions of Px by Py by N−1. Datacube 408-1 may be conceptualized as having N−1 two-dimensional (2D) data matrices each having Px times Py temporal correlation measurement values 506. Each 2D data matrix in datacube 408-1 corresponds to a particular pairing of frames 302. For example, a first 2D data matrix in datacube 408-1 includes temporal correlation measurement values 506 generated based on sample values included in frames 302-1 and 302-2, a second 2D data matrix in datacube 408-1 includes temporal correlation measurement values 506 generated based on sample values included in frames 302-2 and 302-3, etc.

Processor 108 may similarly obtain and include temporal correlation measurement values 506 in datacubes for every other pixel region that fits within frames 302. For example, processor 108 may obtain temporal correlation measurement values 506 for pixel region 404-2, and include these temporal correlation measurement values 506 in a datacube 408-2 (also referred to as datacube $d_{12}$). Likewise, processor 108 may obtain temporal correlation measurement values 506 for pixel region 404-3, and include these temporal correlation measurement values 506 in a datacube 408-3 (also referred to as datacube $d_{13}$).

Processor 108 may apply spatial-based correlation measurement operations to the temporal correlation measurement values 506 included in each datacube 408. For example, with respect to datacube 408-1, processor 108 may apply the spatial-based correlation measurement operations by processing together all of the temporal correlation measurement values included in a particular 2D data matrix included in datacube 408-1.

To illustrate, reference is again made to FIG. 5. As illustrated by arrows 508-1 and 508-2, processor 108 may process temporal correlation measure value 506-1 with temporal correlation measure value 506-2 (and any other temporal correlation measure values obtained by processor 108 for the pair of frames 302-1 and 302-2) to obtain a first spatial correlation measure value 510-1. Likewise, as illustrated by arrows 508-3 and 508-4, processor 108 may process temporal correlation measure value 506-3 with temporal correlation measure value 506-4 (and any other temporal correlation measure values obtained by processor 108 for the pair of frames 302-2 and 302-3) to obtain a second spatial correlation measure value 510-2. This process may be repeated for each 2D data matrix included in datacube 408-1.

Processor 108 may process temporal correlation measure values 506 with each other in any suitable manner to obtain a spatial correlation measure value 510. For example, processor 108 may compute a variance of the temporal correlation measure values 506.

Processor 108 may combine each of the spatial correlation measure values generated for a datacube 408 into a single spatiotemporal correlation measure value for the pixel region 404 associated with the datacube 408. For example, processor 108 may combine spatial correlation measure value 510-1, spatial correlation measure value 510-2, and any other spatial correlation measure value obtained for pixel region 404-1 into a single spatiotemporal correlation measure value for pixel region 404-1. This combination may be performed in any suitable way. For example, processor 108 may add spatial correlation measure value 510-1, spatial correlation measure value 510-2, and any other spatial correlation measure value obtained for pixel region 404-1 together to obtain the single spatiotemporal correlation measure value for pixel region 404-1.

In general, the transformation of temporal correlation measure values in datacube 408-1 to a single spatiotemporal correlation measure value may be represented by $C[d_{11}, dt=1]$, where the function C can include any suitable processing operation. Likewise, the transformation of temporal correlation measure values in datacube 408-2 to a single spatiotemporal correlation measure value may be represented by $C[d_{12}, dt=1]$, the transformation of temporal correlation measure values in datacube 408-3 to a single spatiotemporal correlation measure value may be represented by $C[d_{13}, dt=1]$, etc. One exemplary function C is the sum of spatial variances over time, as describe above and as represented in the following equation: $C(d)=\text{var}[d[x,y,1)]+\text{var}[d[x,y,2)]+ \ldots +\text{var}[d[x,y,N-1)]$, where x and y refer the different pixel locations within a pixel region, and where the sum is over N different frames separated by a particular delay time interval.

The single spatiotemporal correlation measure values derived from datacubes 408 may be included by processor 108 in corresponding locations 406 in correlation map 402. For example, the single spatiotemporal correlation measure value derived from datacube 408-1 may be included in location 406-1, the single spatiotemporal correlation measure value derived from datacube 408-2 may be included in location 406-2, the single spatiotemporal correlation measure value derived from datacube 408-3 may be included in location 406-3, etc. This may be performed in any suitable manner.

Figure 6:
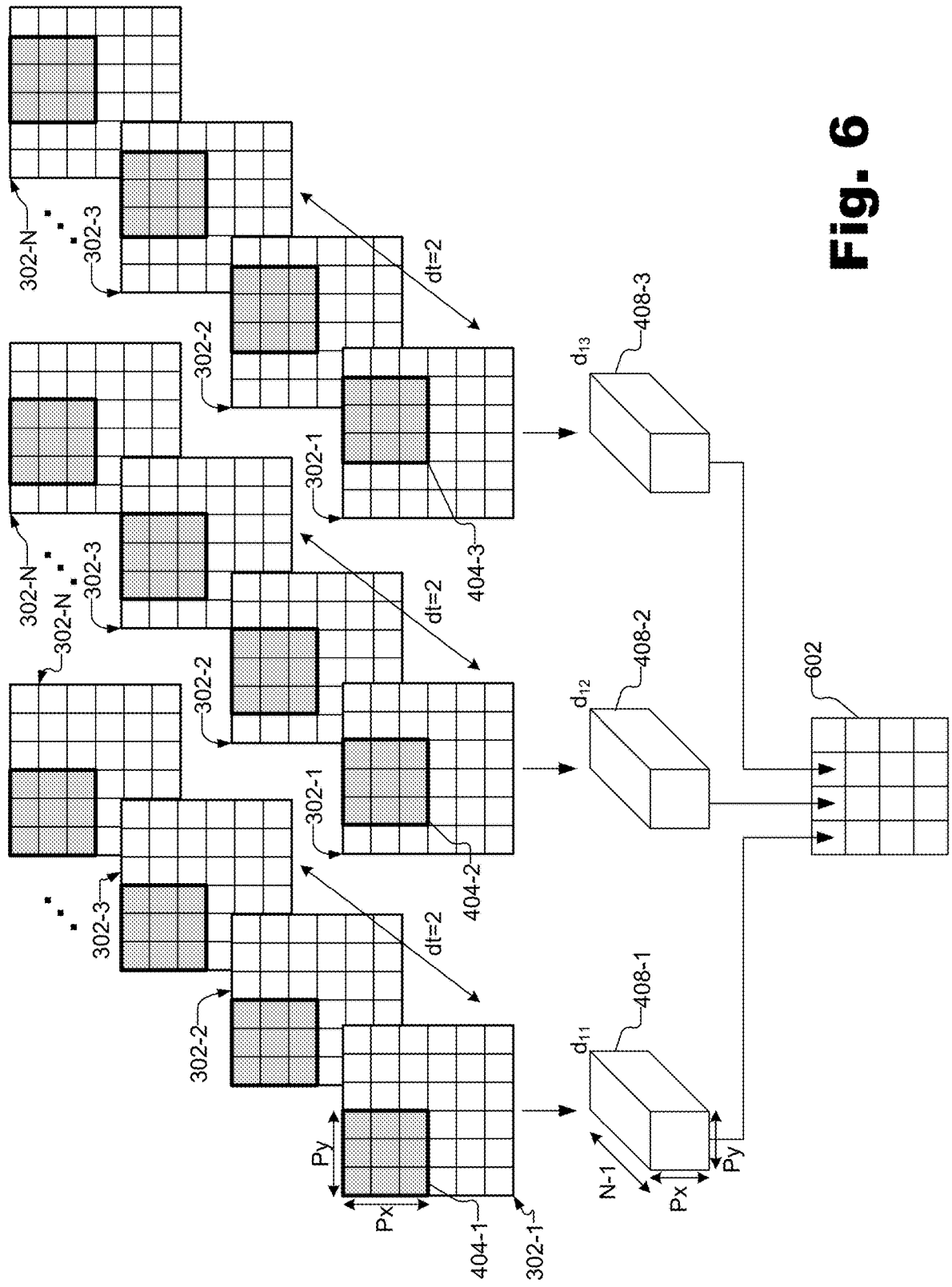
FIG. 6 illustrates an exemplary heuristic that may be performed by a processor on frames to generate a correlation map according to principles described herein.

The process described in FIG. 4 may be repeated for additional delay time intervals to generate additional correlation maps each corresponding to a different delay time interval. For example, FIG. 6 illustrates an exemplary heuristic that may be performed by processor 108 on frames 302 to generate a correlation map 602 that corresponds to a delay time interval of two. In this heuristic, processor 108 may apply temporal-based correlation measurement operations to pairs of frames 302 that are separated by a delay time interval of two (e.g., frames 302-1 and 302-3, frames 302-2 and 302-4 (not shown), etc.).

Any number of correlation maps may be generated by processor 108. For example, processor 108 may generate correlation maps corresponding to delay time intervals of dt=1, dt=2, dt=3, ..., dt=G, where G may be any suitable number (e.g., between 10 and 1000). Here, G is analogous to the maximum temporal extent of a standard decorrelation curve in DCS. The correlation maps generated by processor 108 may be transmitted by processor 108 to any suitable computing device configured to process the data included in the correlation maps (e.g., by using the correlation maps to generate a volumetric reconstruction of brain activity). In some examples, processor 108 may transmit the correlation maps to controller unit 102, which may use the data included in correlation maps to control various aspects of DCS system 102.

Figure 7:
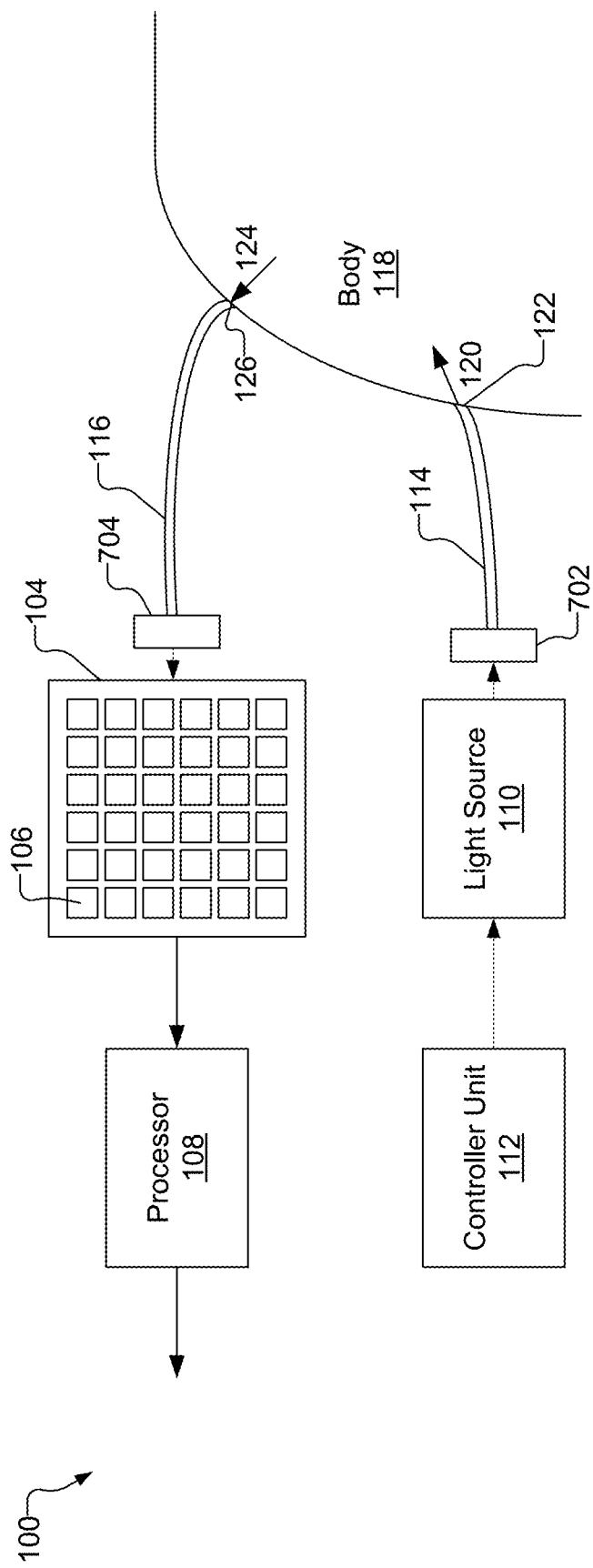
FIG. 7 illustrates an alternative implementation of a DCS system according to principles described herein.

FIG. 7 illustrates an alternative implementation of DCS system 102. FIG. 7 is similar to FIG. 1, except that in FIG. 7, DCS system 102 includes a polarization device 702 and a cross polarizer 704. Polarization device 702 is positioned in an optical path between an output of light source 110 and body 118, and is configured to set a polarization of the light generated by light source 110 to a predetermined state. Cross polarizer 704 is configured to prevent light having the predetermined state from being applied to photodetector array 104. The use of polarization device 702 and cross polarizer 704 may improve the ability to separate signal that arises from the brain as opposed to the scalp and/or skull. This is because light that reflects off the scalp and/or skull likely still has the same polarization state that it had when it was output by light source 110. In contrast, much of the light that enters and emerges from the brain has had its polarization state randomly changed. Hence, by blocking light that has a polarization state that has not changed since being generated by light source 110 from being detected by photodetector array 104, the systems and methods described herein may ensure that the light that is detected by photodetector array 104 has actually entered the brain.

Figure 8:
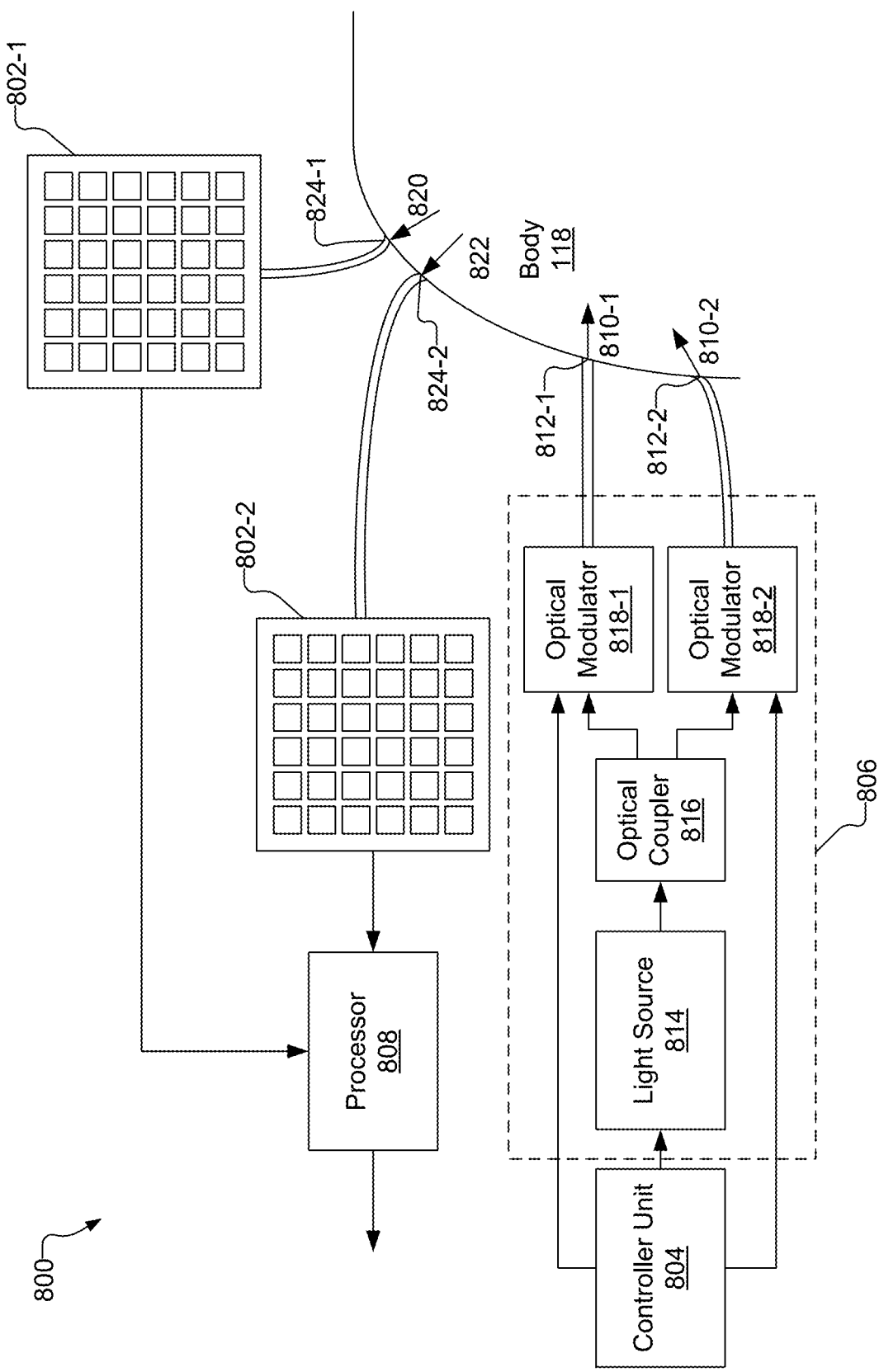
FIG. 8 shows an exemplary DCS system that includes multiple photodetector arrays according to principles described herein.

FIG. 8 shows an exemplary DCS system 800 that includes multiple photodetector arrays 802 (e.g., photodetector array 802-1 and photodetector array 802-1) configured to detect light that exits body 118 at different locations. To facilitate operation of multiple photodetector arrays 802, DCS system 800 includes a controller unit 804 (which may be similar to controller unit 112), a light source assembly 806, and a processor 808 (which may be similar to processor 108).

Light source assembly 806 is configured to generate a first optical beam 810-1 that enters body 118 at a first entry location 812-1 and a second optical beam 810-2 that enters body 118 at a second entry location 812-2. In the example of FIG. 8, light source assembly 806 is implemented by a light source 814 (which may be similar to light source 110), an optical coupler 816, and first and second optical modulators 818-1 and 818-2. Light source 814 is configured to generate a single optical beam. Optical coupler 816 is connected to an output of light source 814 and configured to split the single optical beam into first optical beam 810-1 and second optical beam 810-2.

Optical modulator 818-1 is optically connected to optical coupler 816 and configured to receive optical beam 810-1 and selectively allow optical beam 810-1 to enter body 118 at the first entry location 812-1. Likewise, optical modulator 818-2 is optically connected to optical coupler 816 and configured to receive optical beam 810-2 and selectively allow optical beam 810-2 to enter body 118 at the second entry location 812-2.

As shown, controller unit 804 may be communicatively coupled to optical modulators 818. Controller unit 804 may transmit instructions to optical modulators 818 to cause optical modulators 818 to selectively change the amplitude, phase, and/or polarization state of optical beams 810. In some examples, controller unit 804 may transmit instructions to optical modulator 818-1 that cause optical modulator 818-1 to prevent optical beam 810-1 from entering the body 118 while optical beam 812-2 is entering the body 118. Likewise, controller unit 804 may transmit instructions to optical modulator 818-2 that cause optical modulator 818-2 to prevent optical beam 810-2 from entering the body 118 while optical beam 812-1 is entering the body 118. In this manner, DCS system 800 may ensure that optical beams 810-1 and 810-2 do not interfere one with another.

Photodetector array 802-1 is configured to detect light 820 (e.g., light from either optical beam 810) that exits body 118 at a first exit location 824-1 and output electronic signals representative of the light detected by photodetector array 802-1 as a function of time. Likewise, photodetector array 802-2 is configured to detect light 820 (e.g., light from either optical beam 810) that exits body 118 at a second exit location 824-2 and output electronic signals representative of the light detected by photodetector array 802-2 as a function of time.

Processor 808 is connected to outputs of photodetector arrays 802 and is configured to generate a first correlation map that includes a plurality of spatiotemporal correlation measure values corresponding to the light detected by photodetector array 802-1 and a second correlation map that includes a plurality of spatiotemporal correlation measure values corresponding to the light detected by photodetector array 802-2. This may be performed in any of the ways described herein. The first and second correlation maps (and any other correlation map generated by processor 808 for either photodetector array 802) may be output to a computing device (not shown), which may process the correlation maps in any suitable manner. Likewise, this extension to two photodetector arrays 802 is generalizable to three or more photodetector arrays distributed across the body.

Figure 9:
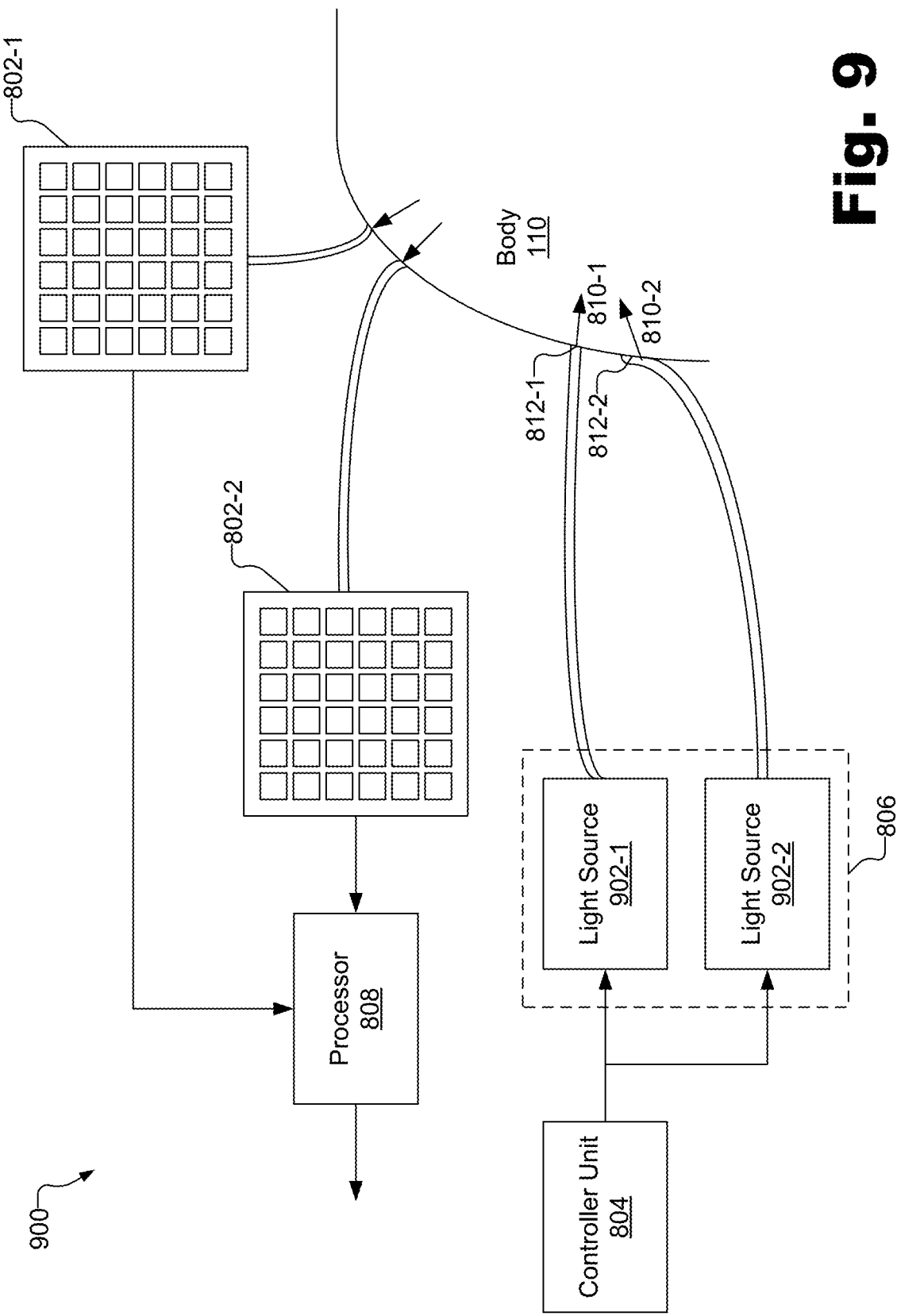
FIG. 9 shows an alternative configuration of the DCS system of FIG. 8 according to principles described herein.

FIG. 9 shows an alternative configuration 900 of DCS system 800. In configuration 900, light source assembly 806 is implemented by multiple light sources 901-1 and 902-2. Light source 902-1 is configured to output optical beam 810-1 and light source 902-2 is configured to output optical beam 810-2. In this configuration, each light source 902 may be controlled by controller unit 804 to output optical beams having different wavelengths and/or other characteristics.

For example, optical beams 810-1 and 810-2 may have different wavelengths. Photodetector arrays 802 may detect this light in series or in parallel and then perform a suitable post-processing step to obtain more information about the decorrelation signal than would be possible from measuring a single wavelength. For example, light sources 902-1 and 902-2 may be turned on one at a time in series and photodetector arrays 802 together with processor 808 may detect the light, digitize the resulting electronic signals, and generate correlation maps for each wavelength. A separate computing device (not shown) may determine a multi-wavelength weighted combination, which may be used to help better isolate decorrelation signal that arises from only scattering changes, as opposed to scattering and absorption and blood flow changes. This extension to two light sources 902 is generalizable to three or more light sources distributed across the body.

Figure 10:
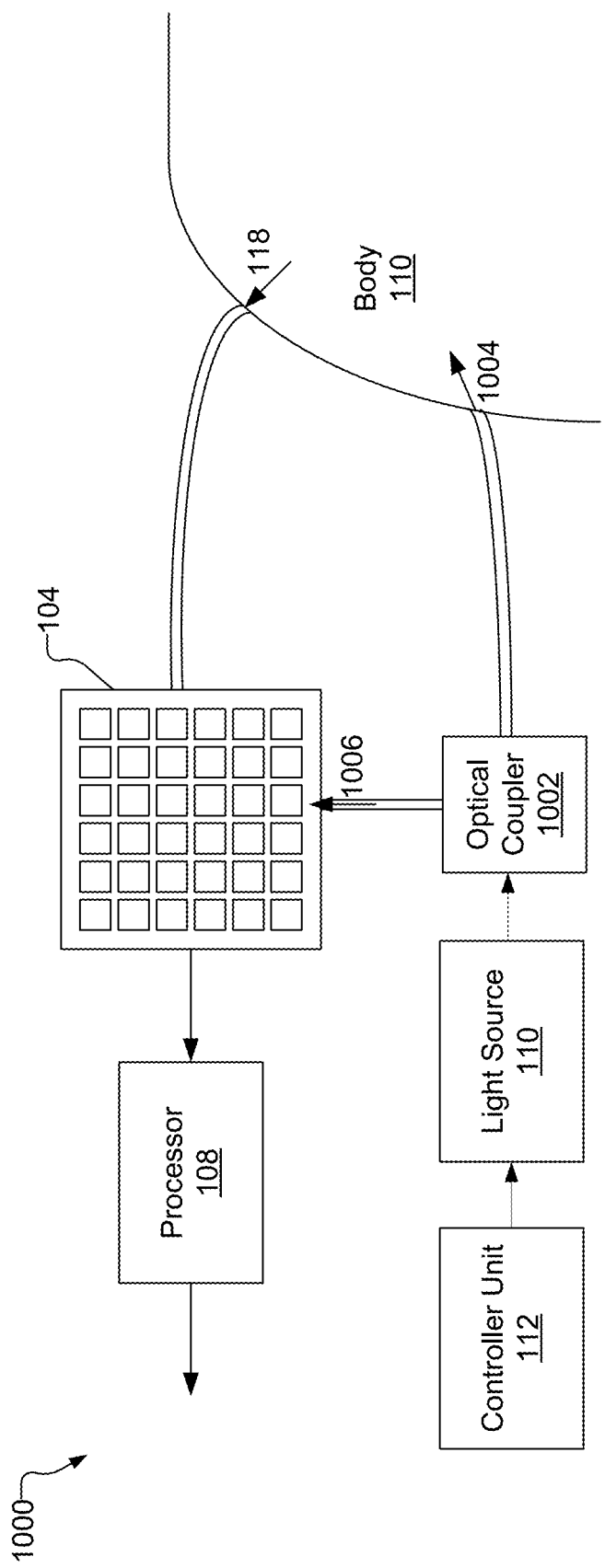
FIG. 10 illustrates an exemplary configuration in which an optical coupler is configured to split an optical beam output by a light source into a sample and reference beam according to principles described herein.

FIG. 10 illustrates an exemplary configuration in which an optical coupler 1002 is configured to split an optical beam output by light source 110 such that a first optical beam 1004 (i.e., a sample beam) enters body 110 and a second optical beam 1006 (i.e., a reference beam) is applied directly to photodetector array 104. Optical beam 1006 may be referred to as a flat reference beam and may be configured to boost a signal level of the light 118 that exits the body 110 above the noise floor so that photodetector array 104 may more easily detect light 118.

In some examples, any of the photodetector arrays describe herein may be included as part of a wearable assembly configured to be positioned on a body of a user. For example, the wearable assembly may be worn on the head of a user.

Figure 11:
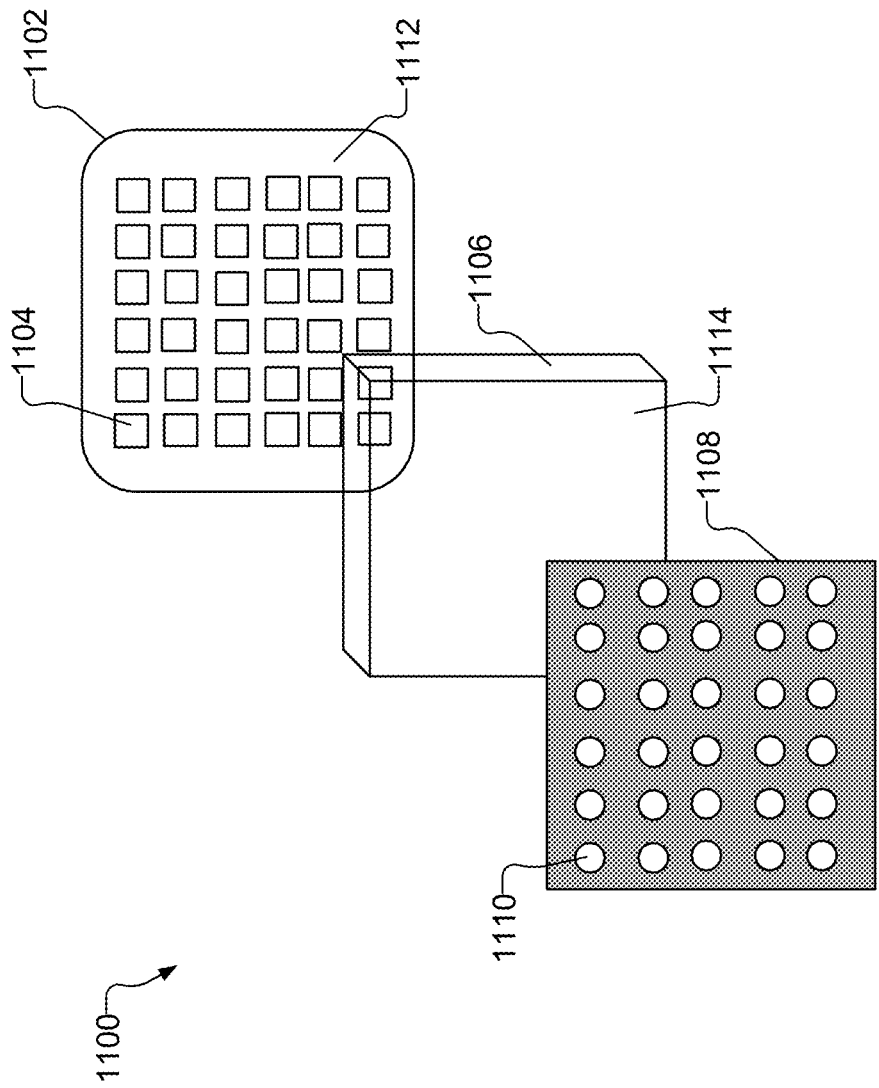
FIG. 11 is an exploded view of an exemplary non-invasive wearable assembly according to principles described herein.

To illustrate, FIG. 11 is an exploded view of an exemplary non-invasive wearable assembly 1100. As shown, wearable assembly 1100 includes a photodetector array 1102 that has a plurality of photodetectors (e.g., photodetector 1104), an optical spacer 1106, and a pinhole array 1108 that has a plurality of pinholes (e.g., pinhole 1110).

Optical spacer 1106 may be implemented by a sheet of glass or other flexible transparent material of finite thickness and may be attached to a front surface 1112 of photodetector array 1102.

Pinhole array 1108 may be made out of any suitable material and may be attached to a front surface 1114 of optical spacer 1106. The pinholes of pinhole array 1108 may be configured to be aligned with the photodetectors of photodetector array 1102. Hence, if photodetector array 1102 is a K by L array that includes K times L photodetectors, pinhole array 1108 is also a K by L array that includes K times L pinholes.

The pinholes of pinhole array 1108 are configured to be in physical contact with the body and allow only a certain amount of light to be incident upon each of the photodetectors in photodetector array 1102. In other words, pinhole array 1108 blocks a certain amount of the speckle pattern from being detected by each of the photodetectors in photodetector array 1102. By blocking light, pinhole array 1108 may reduce the number of speckles that fall upon each photodetector, which may improve the contrast of spatiotemporal correlation.

Figure 12:
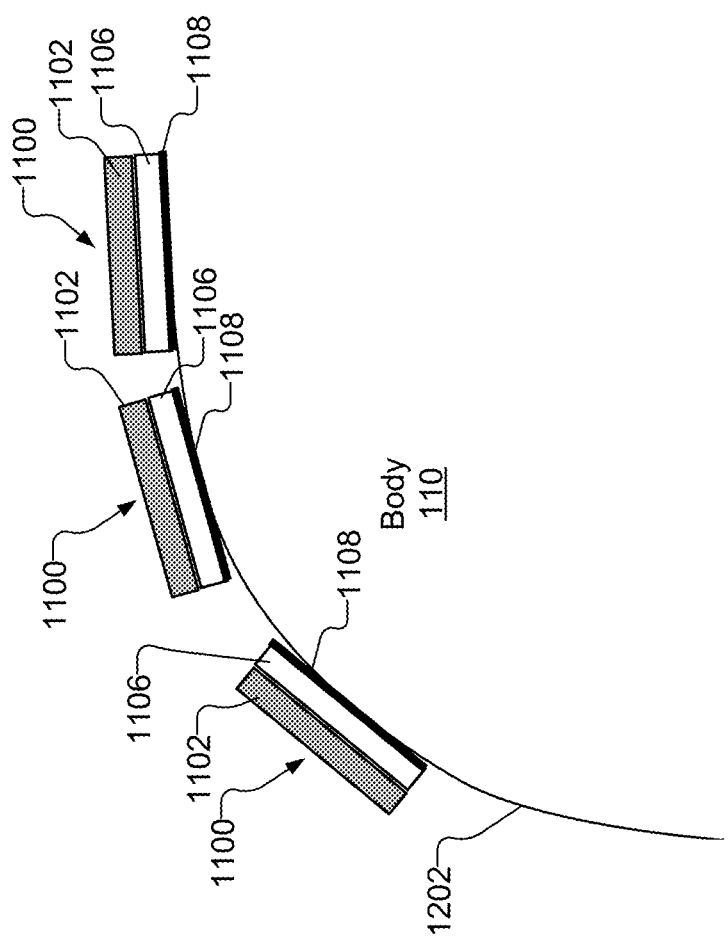
FIG. 12 shows wearable assemblies positioned on an outer surface of a body according to principles described herein.

FIG. 12 shows three wearable assemblies 1100 positioned on an outer surface 1202 of body 110. As shown, in this configuration, there is no need for optical fibers to be included to direct light exiting body 110 to photodetector arrays 1102.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 13:
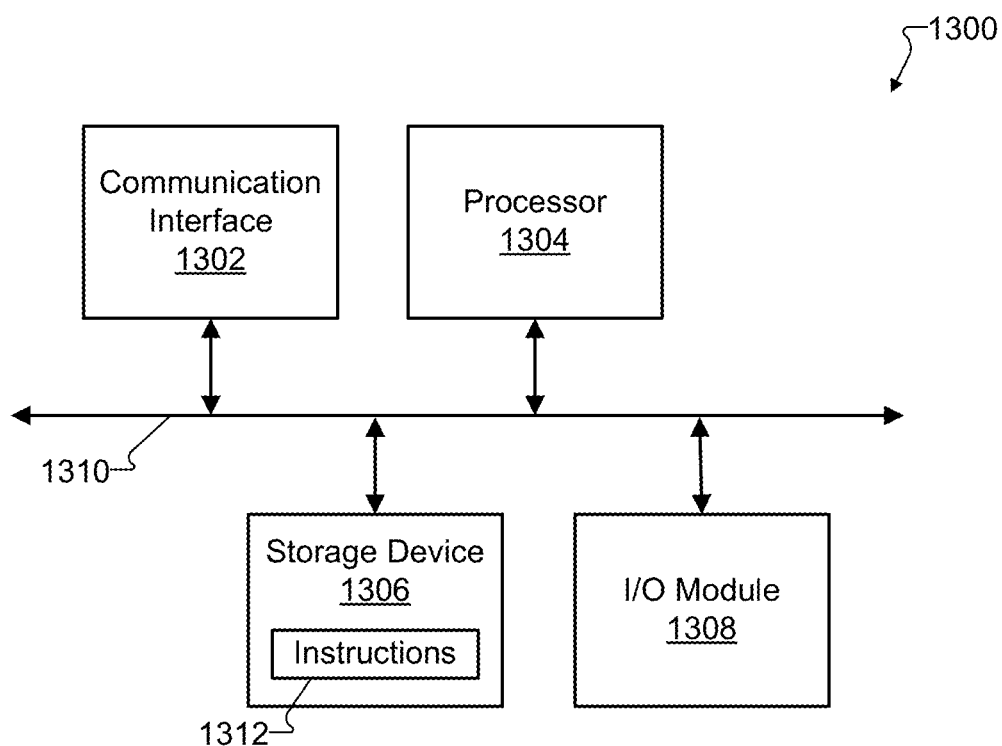
FIG. 13 illustrates an exemplary computing device according to principles described herein.

FIG. 13 illustrates an exemplary computing device 1300 that may be specifically configured to perform one or more of the processes described herein. As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1300. For example, processor 108, processor 108, controller unit 112, and/or controller unit 804 may be implemented by processor 1304.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
an assembly comprising:
a K by L photodetector array comprising a plurality of photodetectors and configured to
detect light that exits a body at a second location after the light enters the body at a first location different than the second location and scatters within the body, and
output a plurality of electronic signals representative of the detected light as a function of time, where each photodetector included in the photodetector array is configured to output a different one of the electronic signals;
a pinhole array, the pinhole array having a K by L array of pinholes configured to be aligned with the photodetectors, the pinhole array configured to allow a certain amount of light to be incident upon each of the photodetectors;

an optical spacer attached to a front surface of the photodetector array, wherein the pinhole array is attached to a front surface of the optical spacer; and a processor coupled to an output of the photodetector array and configured to generate a correlation map that includes a plurality of spatiotemporal correlation measure values corresponding to the light detected by the photodetector array.

2. The system of claim 1, wherein the processor is configured to generate the correlation map by:

sampling the electronic signals output by the photodetector array at a plurality of delay times during a predetermined time period to generate a sequence of frames each corresponding to a different delay time in the plurality of delay times, where each of the frames includes K times L digital sample values at K by L pixel locations that correspond to locations of the photodetectors within the photodetector array;

applying a plurality of temporal-based and spatial-based correlation measurement operations to the sample values in each of the frames;

generating, based on the application of the temporal-based and spatial-based correlation measurement operations to the sample values in each of the frames, the plurality of spatiotemporal correlation measure values for the light detected by the photodetector array; and including the plurality of spatiotemporal correlation measure values in the correlation map, the correlation map corresponding to a predetermined delay time interval that represents a difference between two delay times within the plurality of delay times.

3. The system of claim 2, wherein:

the processor is configured to apply the plurality of temporal-based and spatial-based correlation measurement operations to the sample values in each of the frames by applying the plurality of temporal-based and spatial-based correlation measurement operations to sample values included in a plurality of overlapping pixel regions in each of the frames, where
each of the pixel regions includes Px by Py pixel locations, and
Px times Py is greater than one; and the plurality of spatiotemporal correlation measure values each correspond to a different one of the overlapping pixel regions.

4. The system of claim 2, wherein:

the predetermined delay time interval is one;

a first pixel region in the overlapping pixel regions includes a first pixel location and a second pixel location;

each of the frames includes a first sample value corresponding to the first pixel location and a second sample value corresponding to the second pixel location;

the frames include a first frame corresponding to a first delay time, a second frame corresponding to a second delay time immediately subsequent to the first delay time, and a third frame corresponding to a third delay time immediately subsequent to the second delay time; and the processor is configured to apply the temporal-based correlation measurement operations by
processing the first sample value in the first frame with the first sample value in the second frame to obtain a first temporal correlation measure value for the first pixel location, processing the first sample value in the second frame with the first sample value in the third frame to obtain a second temporal correlation measure value for the first pixel location, processing the second sample value in the first frame with the second sample value in the second frame to obtain a first temporal correlation measure value for the second pixel location, and processing the second sample value in the second frame with the second sample value in the third frame to obtain a second temporal correlation measure value for the second pixel location.

5. The system of claim 4, wherein the processing of the first sample value in the first frame with the first sample value in the second frame to obtain the first temporal correlation measure value for the first pixel location comprises multiplying the first sample value in the first frame with the first sample value in the second frame.

6. The system of claim 4, wherein the processor is configured to apply the spatial-based correlation measurement operations by:

processing the first temporal correlation measure value for the first pixel location with the first temporal correlation measure value for the second pixel location to obtain a first spatial correlation measure; and processing the second temporal correlation measure value for the first pixel location with the second temporal correlation measure value for the second pixel location to obtain a second spatial correlation measure.

7. The system of claim 6, wherein the processing of the first temporal correlation measure value for the first pixel location with the first temporal correlation measure value for the second pixel location comprises computing a variance of the first temporal correlation measure value for the first pixel location and the first temporal correlation measure value for the second pixel location.

8. The system of claim 7, wherein the processor is configured to:

combine the first and second spatial correlation measure values to obtain a single spatiotemporal correlation measure value for the first pixel region; and include the single spatiotemporal correlation measure value in the correlation map at a location that corresponds to the first pixel region.

9. The system of claim 8, wherein the combining of the first and second spatial correlation measure values comprises adding the first and second spatial correlation measure values.

10. The system of claim 8, wherein:

a second pixel region in the overlapping pixel regions includes the second pixel location and a third pixel location;

each of the frames further includes a third sample value corresponding to the third pixel location; and the processor is further configured to apply the temporal-based correlation measurement operations by
processing the third sample value in the first frame with the third sample value in the second frame to obtain a first temporal correlation measure value for the third pixel location, and processing the third sample value in the second frame with the third sample value in the third frame to obtain a second temporal correlation measure value for the third pixel location.

11. The system of claim 10, wherein the processor is further configured to apply the spatial-based correlation measurement operations by:

processing the first temporal correlation measure value for the second pixel location with the first temporal correlation measure value for the third pixel location to obtain a third spatial correlation measure; and processing the second temporal correlation measure value for the second pixel location with the second temporal correlation measure value for the third pixel location to obtain a fourth spatial correlation measure.

12. The system of claim 11, wherein the processor is further configured to:

combine the third and fourth spatial correlation measure values to obtain a single spatiotemporal correlation measure value for the second pixel region; and include the single spatiotemporal correlation measure value for the second pixel region in the correlation map at a location that corresponds to the second pixel region.

13. The system of claim 4, wherein the frames further include a fourth frame corresponding to a fourth delay time immediately subsequent to the third delay time and a fifth delay time immediately subsequent to the fourth delay time, and wherein the processor is further configured to:

generate, based on the application of the temporal-based and spatial-based correlation measurement operations to the sample values in each of the frames, an additional plurality of spatiotemporal correlation measure values for the light detected by the photodetector array; and include the additional plurality of spatiotemporal correlation measure values in an additional correlation map that corresponds to a predetermined delay time interval equal to two.

14. The system of claim 13, wherein the processor is configured to apply the temporal-based correlation measurement operations to generate the additional correlation map by:

processing the first sample value in the first frame with the first sample value in the third frame to obtain a first temporal correlation measure value associated with the additional correlation map for the first pixel location;

processing the first sample value in the third frame with the first sample value in the fifth frame to obtain a second temporal correlation measure value associated with the additional correlation map for the first pixel location;

processing the second sample value in the first frame with the second sample value in the third frame to obtain a first temporal correlation measure value associated with the additional correlation map for the second pixel location; and processing the second sample value in the third frame with the second sample value in the fifth frame to obtain a second temporal correlation measure value associated with the additional correlation map for the second pixel location.

15. The system of claim 14, wherein the processor is configured to apply the spatial-based correlation measurement operations to generate the additional correlation map by:

processing the first temporal correlation measure value associated with the additional correlation map for the first pixel location with the first temporal correlation measure value associated with the additional correlation map for the second pixel location to obtain a first spatial correlation measure associated with the additional correlation map; and processing the second temporal correlation measure value associated with the additional correlation map for the first pixel location with the second temporal correlation measure value associated with the additional correlation map for the second pixel location to obtain a second spatial correlation measure associated with the additional correlation map.

16. The system of claim 15, wherein the processor is further configured to:

combine the first and second spatial correlation measure values associated with the additional correlation map to obtain a single spatiotemporal correlation measure value associated with the additional correlation map for the first pixel region; and include the single spatiotemporal correlation measure value associated with the additional correlation map in the additional correlation map at a location that corresponds to the first pixel region.

17. The system of claim 1, wherein the light that enters the body has a coherence length of at least 5 centimeters.

18. The system of claim 1, further comprising a light source configured to generate the light that enters the body.

19. The system of claim 18, wherein the light source is a high-coherence laser diode.

20. The system of claim 18, further comprising a polarization device positioned in an optical path between an output of the light source and the body, the polarization device configured to set a polarization of the light generated by the light source to a predetermined state.

21. The system of claim 18, further comprising a single-mode optical fiber configured to be connected to an output of the light source and to the body at the first location, wherein the light generated by the light source travels to the body by way of the single-mode optical fiber.

22. The system of claim 18, further comprising a controller unit configured to control the light source by:

turning on and off the light source; and setting an intensity of the light generated by the light source.

23. The system of claim 18, further comprising an optical coupler connected to an output of the light source, the optical coupler configured to split the light into a first optical beam that enters the body at the first location and a second optical beam that is applied directly to the photodetector array, the second optical beam configured to boost a signal level of the light that exits the body at the second location.

24. The system of claim 1, wherein the photodetectors are single photon avalanche diode (SPAD) circuits.

25. The system of claim 1, wherein the assembly is wearable and configured to be positioned on the body.

26. The system of claim 1, wherein the pinhole array is configured to be in physical contact with the body.

* * * * *